United States Patent
Ueda et al.

(10) Patent No.: US 9,322,860 B2
(45) Date of Patent: Apr. 26, 2016

(54) ELECTRICAL RESISTANCE MEASURING DEVICE FOR TIRE

(71) Applicant: MITSUBISHI HEAVY INDUSTRIES MACHINERY TECHNOLOGY CORPORATION, Hiroshima-shi, Hiroshima (JP)

(72) Inventors: Tatsuya Ueda, Hiroshima (JP); Jiro Agawa, Hiroshima (JP)

(73) Assignee: MITSUBISHI HEAVY INDUSTRIES MACHINERY TECHNOLOGY CORPORATION, Hiroshima (JP)

(*) Notice: Subject to any disclaimer, the term of this patent is extended or adjusted under 35 U.S.C. 154(b) by 0 days.

(21) Appl. No.: 14/374,013

(22) PCT Filed: Jun. 20, 2013

(86) PCT No.: PCT/JP2013/066935
§ 371 (c)(1),
(2) Date: Jul. 23, 2014

(87) PCT Pub. No.: WO2014/069039
PCT Pub. Date: May 8, 2014

(65) Prior Publication Data
US 2015/0241491 A1 Aug. 27, 2015

(30) Foreign Application Priority Data
Oct. 31, 2012 (JP) ................. 2012-240521

(51) Int. Cl.
*G01R 27/08* (2006.01)
*G01R 27/02* (2006.01)
(Continued)

(52) U.S. Cl.
CPC .............. *G01R 27/02* (2013.01); *G01M 17/02* (2013.01); *G01N 27/041* (2013.01); *G01R 27/20* (2013.01); *G01R 31/006* (2013.01)

(58) Field of Classification Search
CPC ........ G01R 27/10; G01R 27/12; G01R 27/14; G01R 31/006; G01N 2033/0085; G01M 17/02
See application file for complete search history.

(56) References Cited

U.S. PATENT DOCUMENTS 4,896,531 A * 1/1990 Hayes .................. G01M 17/02
73/146
6,201,400 B1 * 3/2001 Lind .................. G01R 27/2676
324/601

(Continued)

FOREIGN PATENT DOCUMENTS

CN 2809651 Y 8/2006
CN 101176004 A 5/2008
(Continued)

OTHER PUBLICATIONS

Office Action mailed May 19, 2015, corresponding to Korean patent application No. 10-2014-7016969.
(Continued)

*Primary Examiner* — Huy Q Phan
*Assistant Examiner* — Dustin Dickinson
(74) *Attorney, Agent, or Firm* — Kanesaka Berner and Partners LLP

(57) ABSTRACT

An electrical resistance measuring device for a tire (T) that measures the electrical resistance from a bead portion (71) to a tread portion (70) and includes a measuring tip (5a) that is curvedly deformable along the shape of the tire (T).

6 Claims, 8 Drawing Sheets

(51) Int. Cl.
*G01M 17/02* (2006.01)
*G01N 27/04* (2006.01)
*G01R 27/20* (2006.01)
*G01R 31/00* (2006.01)

(56) References Cited

U.S. PATENT DOCUMENTS

| | | | |
|---|---|---|---|
| 6,802,212 | B2 | 10/2004 | Farne |
| 7,808,256 | B2 | 10/2010 | Murakami et al. |
| 2004/0237639 | A1* | 12/2004 | Bandou ............... G01N 27/60 73/146 |
| 2005/0175146 | A1* | 8/2005 | Uchida ............... G01N 23/04 378/61 |
| 2009/0072842 | A1* | 3/2009 | Murakami ........... B60C 19/08 324/691 |
| 2009/0126844 | A1* | 5/2009 | Nakamura ........... B60C 1/00 152/524 |

FOREIGN PATENT DOCUMENTS

| | | |
|---|---|---|
| CN | 101322865 A | 12/2008 |
| JP | 10170467 A | 6/1998 |
| JP | 2002164137 A | 6/2002 |
| JP | 2005274255 A | 10/2005 |
| JP | 2006317380 A | 11/2006 |
| JP | 2008145346 A | 6/2008 |
| JP | 4150108 B2 | 9/2008 |
| JP | 2008247068 A | 10/2008 |
| KR | 10-2012-0092965 A | 8/2012 |

OTHER PUBLICATIONS

International Search Report mailed Jul. 30, 2013, corresponding to International application No. PCT/JP2013/066935.
Written Opinion mailed Jul. 30, 2013, corresponding to International application No. PCT/JP2013/066935.
Office Action dated Jul. 8, 2015, corresponding to Taiwanese patent application No. 103114521, for which an explanation of the relevance is attached.
Office Action dated Jul. 30, 2015, corresponding to Chinese patent application No. 2013800058082, for which an explanation of the relevance is attached.

* cited by examiner

ELECTRICAL RESISTANCE MEASURING DEVICE FOR TIRE

TECHNICAL FIELD

Related Applications

The present invention relates to an electrical resistance measuring device for a tire.

The referenced application is a National Phase of PCT/JP2013/066935 filed Jun. 20, 2013 and claims priority to Japanese Patent Application No. 2012-240521, filed Oct. 31, 2012, the content of which is incorporated herein by reference.

BACKGROUND ART

Generally, vehicles, such as an automobile, are designed so that, when electrically charged, the electric charges thereof are transferred to the ground via the tires. Thus, in order to allow the electrical charges to be stably transferred to the ground, an inspection process of inspecting the electrical resistance between an inner peripheral portion of a tire and an outer peripheral portion thereof may be performed until shipment after processes, such as vulcanization molding of the tire, are completed. In this inspection process, a variation may be caused in the measured values of the electrical resistance due to a variation in the contact resistance between a measuring tip and a tread portion of the tire. Therefore, a technique of contriving the shape, number, or the like of the measuring tip to stably bring the tire and the measuring tip into contact with each other is suggested (for example, refer to PTLs 1 and 2).

CITATION LIST

Patent Literature

[PTL 1] Japanese Unexamined Patent Application Publication No. 2006-317380
[PTL 2] Japanese Patent No. 4150108

SUMMARY OF INVENTION

Technical Problem

The tread portion or the like of the tire may be obtained by blending a material, such as silica, in which electrical resistance becomes high in order to improve rolling resistance. When the electrical resistance of the tread portion becomes high in this manner, the tire is electrified with charges to be generated on a vehicle, and the charges are not easily transferred to the ground. Therefore, the charges may be easily transferred to the ground by partially arranging a material with low electrical resistance between a shoulder portion and a center portion of the tread portion that comes into contact with the ground. This material with low electrical resistance is generally formed in the shape of a ring over the whole circumference of the tread portion of the tire.

However, the above-described material with low electrical resistance for the tire often varies in arrangement depending on specifications, such as size and shape, manufacturing deviation, or the like. Additionally, the above-described material with low electrical resistance for the tire may not be able to be visually determined. Therefore, when the inspection of the electrical resistance of tires is to be automated, in a tread portion of a tire to be used as an object to be inspected, for example, an adjustment process of confirming a place where the material with low electrical resistance is arranged, to change the position and angle of a measuring tip on the outer peripheral side, is required. As a result, burden on an operator increases.

The invention provides an electrical resistance measuring device for a tire that can stably measure the electrical resistance on tires to be measured having different specifications, without adjusting a measuring tip.

Solution to Problem

According to a first aspect of the invention, there is provided an electrical resistance measuring device for a tire that measures electrical resistance from an inner peripheral portion of the tire to an outer peripheral portion thereof. The electrical resistance measuring device includes a measuring tip that is curvedly deformable along the shape of the tire.

In an electrical resistance measuring device for a tire according to a second aspect of the invention, the measuring tip in the electrical resistance measuring device for a tire of the first aspect may include an inner-peripheral-side measuring tip that is arranged on an inner peripheral side of the tire and is capable of coming into contact with the inner peripheral portion; and an outer-peripheral-side measuring tip that is arranged on an outer peripheral side of the tire and is capable of coming into contact with the outer peripheral portion. Moreover, the outer-peripheral-side measuring tip may be curvedly deformable along the shape of the tire from a central portion of the outer peripheral portion to a shoulder portion thereof in a width direction of the tire.

In an electrical resistance measuring device for a tire according to a third aspect of the invention, the outer-peripheral-side measuring tip in the electrical resistance measuring device for a tire of the first or second aspect may be a linear electric conductor that is arranged to incline so that an upper portion is located further toward a radial outer side of the tire than a lower portion.

In an electrical resistance measuring device for a tire according to a fourth aspect of the invention, in the electrical resistance measuring device for a tire of the second or third aspect, the outer-peripheral-side measuring tip may be elastically deformable, and may come into contact with the outer peripheral portion in an elastically deformed state.

In an electrical resistance measuring device for a tire according to a fifth aspect of the invention, the electrical resistance measuring device for a tire of any one aspect of the second to fourth aspects may be provided with two of the outer-peripheral-side measuring tips and one of the inner-peripheral-side measuring tip.

In an electrical resistance measuring device for a tire according to a sixth aspect of the invention, the electrical resistance measuring device for a tire of any one aspect of the second to fifth aspects may further include a measuring tip spacing adjusting mechanism that creates the distance between the outer-peripheral-side measuring tip and the inner-peripheral-side measuring tip in a floating state.

In an electrical resistance measuring device for a tire according to a seventh aspect of the invention, the electrical resistance measuring device for a tire of any one aspect of the second to sixth aspects may further include a displacement mechanism that displaces the outer-peripheral-side measuring tip and the inner-peripheral-side measuring tip so as to approach and separate from the tire.

Advantageous Effects of Invention

According to the above-described electrical resistance measuring device for a tire, electrical resistance can be stably

DESCRIPTION OF EMBODIMENTS

Hereinafter, a preferred embodiment of the invention will be described with reference to the drawings.

Figure 1:
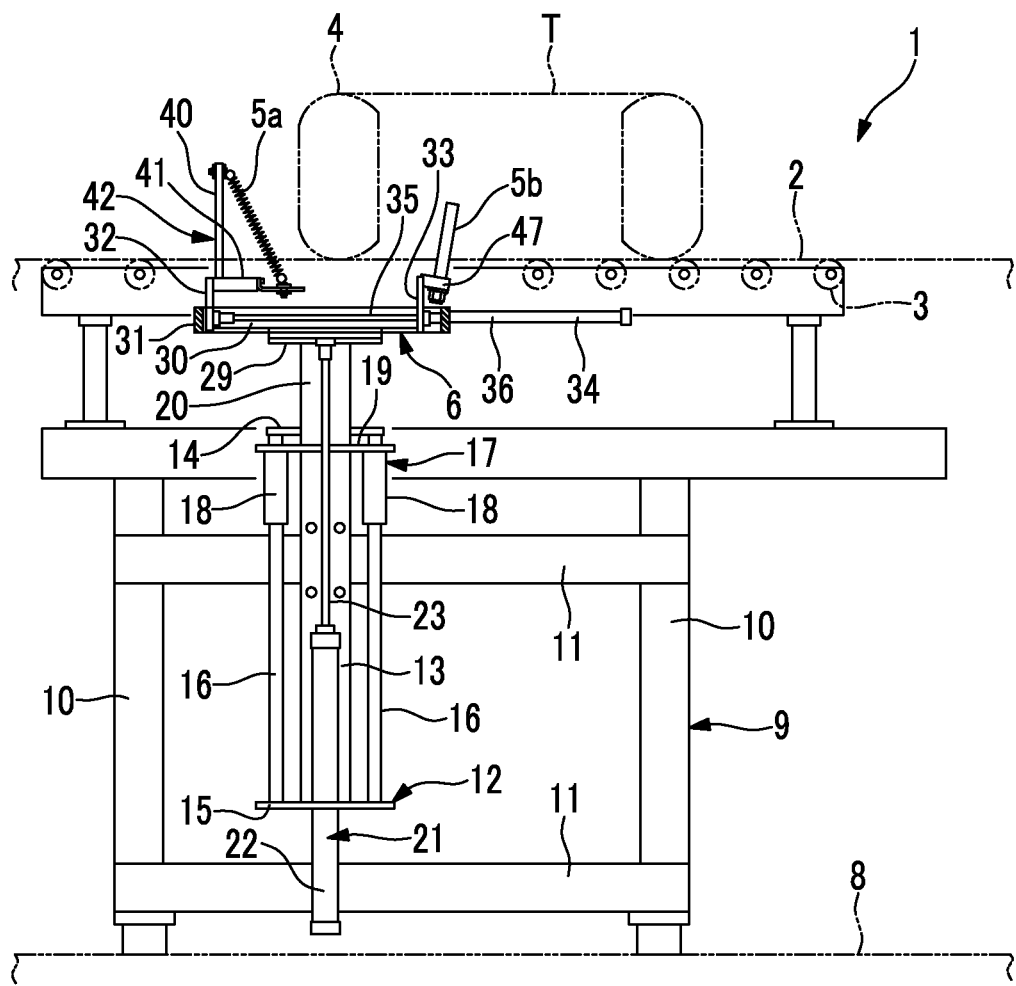
FIG. 1 is a front view of an electrical resistance measuring device for a tire in an embodiment of the invention.

FIG. 1 is a configuration view showing the schematic configuration of an electrical resistance measuring device 1 of this embodiment.

As shown in FIG. 1, the electrical resistance measuring device 1 is arranged on an inspection line (not shown) of a vulcanized tire T, and has a roller conveyor 2 that conveys the tire T. The roller conveyor 2 includes a plurality of rotatable rollers 3 that are arrayed in a conveying direction, and includes the rollers that are separated from each other on both sides of the roller conveyor 2 in a width direction (hereinafter simply referred to as a width direction). The roller conveyor 2 is allowed to convey the tire T in a state where sidewalls 4 of the tire are turned to an up-and-down direction.

The electrical resistance measuring device 1 includes a measuring tip unit (measuring tip spacing adjusting mechanism) 6 having an outer-peripheral-side measuring tip 5a and an inner-peripheral-side measuring tip 5b for measuring the electrical resistance of the tire T. The outer-peripheral-side measuring tip 5a and the inner-peripheral-side measuring tip 5b of the measuring tip unit 6 are allowed to protrude upward from between the portions of the roller conveyor 2 that are separated from each other in the width direction. For the sake of convenience of illustration, the rollers 3, which overlap the measuring tip unit 6 as seen from the front, are omitted in FIG. 1.

The roller conveyor 2 is installed on a platform 9 erected on a floor 8. The platform 9 includes a plurality of legs 10 that extend in the up-and-down direction. Additionally, the platform 9 includes beams 11 that are attached so as to stretch between the adjacent legs 10, and extend in the horizontal direction. The beams 11 are respectively provided at upper portions and lower portions of the legs 10. A lifting mechanism (displacement mechanism) 12 for lifting and lowering the measuring tip unit 6 is attached to the upper beam 11. The lifting mechanism 12 includes a base portion 13 that extends in the up-and-down direction. The base portion 13 is fixed to the beam 11 slightly above a central portion in the up-and-down direction via a bracket (not shown).

An upper end of the base portion 13 is formed with an upper supporting plate 14 that extends in the horizontal direction. Additionally, a lower end of the base portion 13 is formed with a lower supporting plate 15 that faces the upper supporting plate 14. Two parallel guide rods 16 that extend in the up-and-down direction are attached between the upper supporting plate 14 and the lower supporting plate 15. The guide rods 16 are arranged on both the outer sides of the base portion 13 in the width direction, respectively.

A guide portion 17 is liftably attached to the guide rods 16. The guide portion 17 includes two guide tubes 18 through which the guide rods 16 are inserted, and a frame portion 19 that connects upper end portions of the guide tubes 18. Additionally, the frame portion 19 is formed with a supporting arm 20 that extends upward. An upper end of the supporting arm 20 is fixed to a lower surface of the above-described measuring tip unit 6.

The lifting mechanism 12 includes a fluid pressure cylinder 21 as a driving source that lifts and lowers the measuring tip unit 6. The fluid pressure cylinder 21 includes an outer tube 22 that extends in the up-and-down direction, and an inner rod 23 of the outer tube 22 that extends upward. The outer tube 22 is fixed to the lower supporting plate 15, and an upper end of the inner rod 23 is fixed to the lower surface of the measuring tip unit 6. The fluid pressure cylinder 21 is allowed to advance and retract the inner rod 23 due to a differential pressure caused by supplying and discharging a compressed fluid into a cylinder chamber (not shown) of the outer tube 22.

That is, the measuring tip unit 6 moves downward along the guide rods 16 via the guide portion 17 by displacing the inner rod 23 of the fluid pressure cylinder 21 in a compression direction. This allows the measuring tip unit 6 to move in a downward direction away from the roller conveyor 2.

Additionally, the measuring tip unit 6 moves upward along the guide rods 16 via the guide portion 17 by displacing the inner rod 23 of the fluid pressure cylinder 21 in an extension direction. This allows the measuring tip unit 6 to move upward, that is, in a direction approaching the roller conveyor 2.

The measuring tip unit 6 includes a base plate 29 to which an upper end portion of the above-described inner rod 23 is fixed. A frame body 31 that supports a guide rod 30 that extends in the conveying direction is attached to the base plate 29. Moreover, a first sliding portion 32 and a second sliding portion 33 are slidably attached to the guide rod 30 supported by the frame body 31. A fluid pressure cylinder 34 for a measuring tip is attached to the first sliding portion 32 and the second sliding portion 33, as a driving source that moves these sliding portions relative to each other. An end portion of an inner rod 35 of the fluid pressure cylinder 34 for a measuring tip is fixed to the first sliding portion 32. Additionally, an end portion, on the inner rod 35 side, of an outer tube 36 of the fluid pressure cylinder 34 for a measuring tip is fixed to the second sliding portion 33.

A first support metal fitting 42 substantially formed in an L-shape is fixed to the first sliding portion 32. The first support metal fitting 42 includes a longitudinal frame 40 that extends upward, and a transverse frame 41 that extends in a substantially horizontal direction to the second sliding portion 33 side. Additionally, two outer-peripheral-side measuring tips 5a are attached to the first support metal fitting 42 so as to stretch between an end portion of the longitudinal frame 40 and an end portion of the transverse frame 41. The outer-peripheral-side measuring tips 5a are made of linear electric conductors. In this way, the outer-peripheral-side measuring tips 5a, which are attached so as to stretch between the end portion of the longitudinal frame 40 and the end portion of the transverse frame 41, are arranged in an inclined manner so that upper portions thereof are located further toward a radial outer side of the tire T than lower portions thereof. Additionally, the transverse frame 41 of the first support metal fitting 42 is arranged below a conveying surface of the roller conveyor 2. Accordingly, the outer-peripheral-side measuring tips 5a are arranged so as to extend to below the bottom sidewall 4 of the tire T in a height direction.

Figure 2:
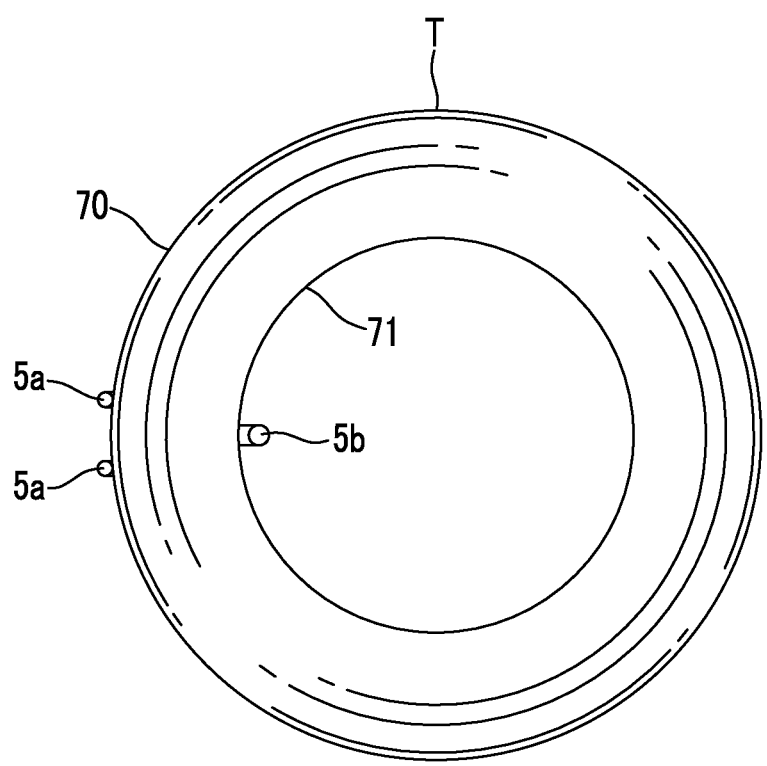
FIG. 2 is a partial cross-sectional view showing main parts of the electrical resistance measuring device.
Figure 3:
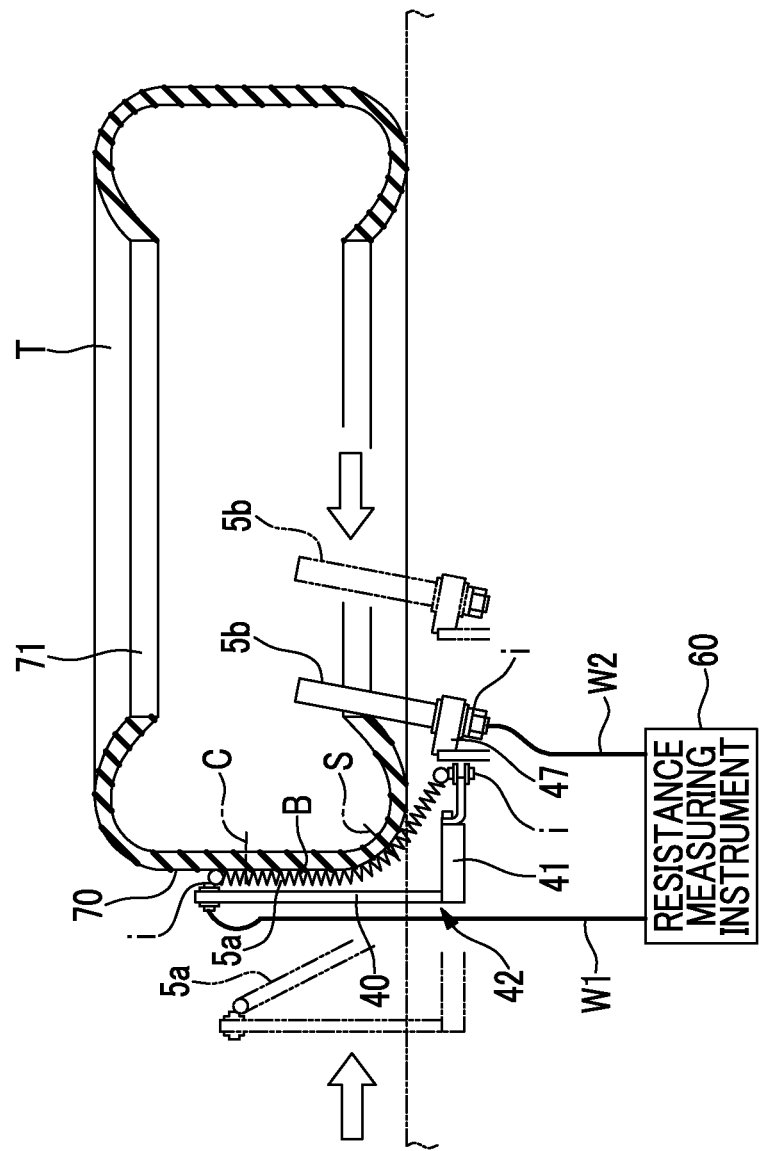
FIG. 3 is a plan view showing an arrangement of an outer-peripheral-side measuring tip and an inner-peripheral-side measuring tip of the electrical resistance measuring device.

As shown in FIG. 2, the two outer-peripheral-side measuring tips 5a are arranged side by side at a predetermined interval in a circumferential direction. Additionally, the inner-peripheral-side measuring tip 5b is arranged on the inner peripheral side between the two outer-peripheral-side measuring tips 5a. Moreover, as shown in FIG. 3, each outer-peripheral-side measuring tip 5a is connected to the first support metal fitting 42 via an insulating member i. That is, the outer-peripheral-side measuring tip 5a and the first support metal fitting 42 are electrically insulated from each other.

As shown in FIGS. 1 and 3, a second support metal fitting 47, which is inclined toward a portion slightly below a side opposite to the first sliding portion 32 from an upper end portion of the second sliding portion 33, is attached to the second sliding portion 33. The inner-peripheral-side measuring tip 5b is provided at the second support metal fitting 47 so as to extend in a vertical direction from an upper surface of the second support metal fitting. The inner-peripheral-side measuring tip 5b is connected to the second support metal fitting 47 via an insulating member i. That is, the inner-peripheral-side measuring tip 5b and the second support metal fitting 47 are electrically insulated from each other.

When the above-described fluid pressure cylinder 34 for a measuring tip is driven in the compression direction, the first sliding portion 32 and the second sliding portion 33 are relatively displaced along the guide rod 30 in directions in which these sliding portions approach each other. As a result, the outer-peripheral-side measuring tip 5a and the inner-peripheral-side measuring tip 5b are displaced in directions in which these measuring tips approach each other.

Additionally, when the fluid pressure cylinder 34 for a measuring tip is driven in the extension direction, the first sliding portion 32 and the second sliding portion 33 are relatively displaced along the guide rod 30 in directions in which these sliding portions are separated from each other. As a result, the outer-peripheral-side measuring tip 5a and the inner-peripheral-side measuring tip 5b are displaced in directions in which these measuring tips are separated from each other.

The fluid pressure cylinder 34 for a measuring tip is supported in a floating state where the inner rod 35 and the outer tube 36 are displaceable together along the guide rod 30. In other words, the fluid pressure cylinder 34 for a measuring tip changes the distance between the outer-peripheral-side measuring tip 5a and the inner-peripheral-side measuring tip 5b in the floating state. For example, the fluid pressure cylinder 34 for a measuring tip is driven in the compression direction so that the outer-peripheral-side measuring tip 5a and the inner-peripheral-side measuring tip 5b sandwich the tire T. Then, first, any one of the outer-peripheral-side measuring tip 5a and the inner-peripheral-side measuring tip 5b abut against the tire T and stop. Next, the other moves relatively in a direction approaching the tire T.

On the contrary, the fluid pressure cylinder 34 for a measuring tip is driven in the extension direction in order to separate the outer-peripheral-side measuring tip 5a and the inner-peripheral-side measuring tip 5b from the tire T. Then, first, any one of the outer-peripheral-side measuring tip 5a and the inner-peripheral-side measuring tip 5b abut against the frame body 31 and stop. Next, the other moves in a direction away from the tire T.

That is, a supporting structure of the fluid pressure cylinder 34 for a measuring tip is configured in the floating state as described above. Accordingly, even if the conveying position of the tire T is slightly shifted, it is possible to sandwich the tire T properly using the outer-peripheral-side measuring tip 5a and the inner-peripheral-side measuring tip 5b.

Additionally, the measuring tip unit 6 is lifted by the driving of the fluid pressure cylinder 21 in a state where a tread portion (outer peripheral portion) 70 of the tire T on the outer peripheral side is arranged on the outer-peripheral-side measuring tip 5a side, and a bead portion (inner peripheral portion) 71 of the tire T on the inner peripheral side is arranged on the inner-peripheral-side measuring tip 5b side. Moreover, by moving the outer-peripheral-side measuring tip 5a and the inner-peripheral-side measuring tip 5b in approaching directions through the driving of the fluid pressure cylinder 34 for a measuring tip, it is possible to sandwich the tire T using the outer-peripheral-side measuring tip 5a and the inner-peripheral-side measuring tip 5b.

As shown in FIG. 3, the outer-peripheral-side measuring tip 5a abuts against the tread portion 70 that is formed on the radial outer side of the tire T. Additionally, the inner-peripheral-side measuring tip 5b abuts against the bead portion 71 formed on the radial inner side of the tire T. The outer-peripheral-side measuring tip 5a is formed of a coil spring B that is elastically deformable and curvable along a tire shape (in other words, the outer shape of the tire T) and has conductivity. Accordingly, when the tire T is pressed, the outer-peripheral-side measuring tip 5a is curved along the shape of the tire T from a center portion C of the tread portion 70 to a shoulder portion S in the width direction (in other words, the axial direction) of the tire T. Here, the shoulder portion S means a portion near the end portion, in the width direction, of the tread portion 70 that touches the ground when a vehicle travels.

If the tire T is made to relatively approach the outer-peripheral-side measuring tip 5a, the outer-peripheral-side measuring tip 5a first abuts against the shoulder portion S of the tire T. Then, the outer-peripheral-side measuring tip 5a is gradually deflected to a side approaching the first support metal fitting 42 from the abutting portion with the relative movement with respect to the tire T. Thereafter, the abutting ranges of the outer-peripheral-side measuring tips 5a are increased to the center portion C side of the tread portion 70. The outer-peripheral-side measuring tip 5a finally abuts against the tread portion 70 of the tire T in a range from the center portion C to the shoulder portion S.

The inner-peripheral-side measuring tip 5b is formed of a conductive rod-shaped member, having sufficient rigidity, which is not deformed when being pressed by the bead portion 71. The inner-peripheral-side measuring tip 5b inclines slightly so that an end portion thereof is arranged further toward to an axial center side of the tire T than a base portion thereof. The inner-peripheral-side measuring tip 5b is adapted such that the bead portion 71 opposite in the width direction to the bead portion 71 that is an object to be measured does not contact the inner-peripheral-side measuring tip 5b, for example, when the width dimension of the tire T is shorter than the length dimension of the inner-peripheral-side measuring tip 5b due to the above shape.

A resistance measuring instrument (measuring unit) 60 is connected to the outer-peripheral-side measuring tip 5a and the inner-peripheral-side measuring tip 5b via wiring lines W1 and W2. The resistance measuring instrument 60 applies a predetermined measuring current between the outer-peripheral-side measuring tip 5a and the inner-peripheral-side measuring tip 5b, and measures a voltage between terminals in such a case, thereby measuring the electrical resistance between the outer-peripheral-side measuring tip 5a and the inner-peripheral-side measuring tip 5b.

Therefore, according to the electrical resistance measuring device 1 of the above-described embodiment, the outer-peripheral-side measuring tip 5a that is curved and deformed simultaneously comes into contact with the range from the center portion C of the tire T to the shoulder portion S thereof. Therefore, a resistance value between a place with the smallest resistance, which extends from the center portion C and the shoulder portion S, and the bead portion 71 can be measured. As a result, with respect to tires T with different specifications, the electrical resistance can be measured by stably bringing the outer-peripheral-side measuring tip 5a into contact with the portion of each tire T from the center portion C to the shoulder portions S without adjusting the outer-peripheral-side measuring tip 5a. Additionally, when the tread portion 70 in which silica or the like is blended is used, even if a portion made of a material having low electrical resistance is partially formed at any position from the center portion C to the shoulder portion S, the electrical resistance between the portion made of the material having low electrical resistance and the bead portion 71 can be measured.

Additionally, simply only by relatively pressing the outer-peripheral-side measuring tip 5a against the tire T, it is possible to bring the outer-peripheral-side measuring tip 5a into electrical contact with the range from the center portion C of the tire T to the shoulder portion S thereof in the width direction. Moreover, since the outer-peripheral-side measuring tip 5a is pressed against the tire T having elasticity, it is possible to keep an excessive contact force from being applied between the outer-peripheral-side measuring tip 5a and the tire T.

Moreover, when the tire T is sandwiched by the outer-peripheral-side measuring tip 5a and the inner-peripheral-side measuring tip 5b, the outer-peripheral-side measuring tip 5a can be stably brought into contact with the tread portion 70 of the tire T by three-point support without being influenced by the size, shape, or the like of the tire T, and the inner-peripheral-side measuring tip 5b can be brought into contact with the bead portion 71 of the tire T.

Additionally, the relative displacement between the outer-peripheral-side measuring tip 5a and the inner-peripheral-side measuring tip 5b is allowed by the measuring tip unit 6. As a result, when the outer-peripheral-side measuring tip 5a has first come into contact with the tire T, the inner-peripheral-side measuring tip 5b can be relatively displaced so as to approach the outer-peripheral-side measuring tip 5a. Additionally, when the inner-peripheral-side measuring tip 5b has first come into contact with the tire T, the outer-peripheral-side measuring tip 5a can be relatively displaced so as to approach the inner-peripheral-side measuring tip 5b. Therefore, by arranging the bead portion 71 and the tread portion 70 of the tire T between the outer-peripheral-side measuring tip 5a and the inner-peripheral-side measuring tip 5b, the tire T can be pressed by the outer-peripheral-side measuring tip 5a and the inner-peripheral-side measuring tip 5b with the same force irrespective of the position or radial dimension of the tire T.

Additionally, by including the lifting mechanism 12, it is possible to bring about a state where the electrical resistance can be measured simply by stopping the tire T being conveyed at a predetermined measurement position and make the outer-peripheral-side measuring tip 5a and the inner-peripheral-side measuring tip 5b approach the tire T. Therefore, it is possible to easily apply the invention to existing facilities.

In addition, the invention is not limited to the above-described embodiment, and design changes can be made without departing from the concept of the invention.

Figure 4A:
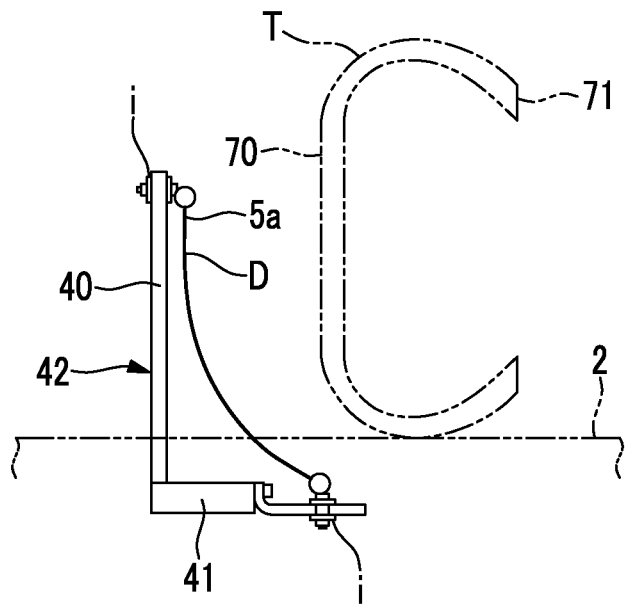
FIG. 4A is a front view of the outer-peripheral-side measuring tip in a first modification example of the embodiment of the invention, in a state before the outer-peripheral-side measuring tip is pressed against a tire.
Figure 4B:
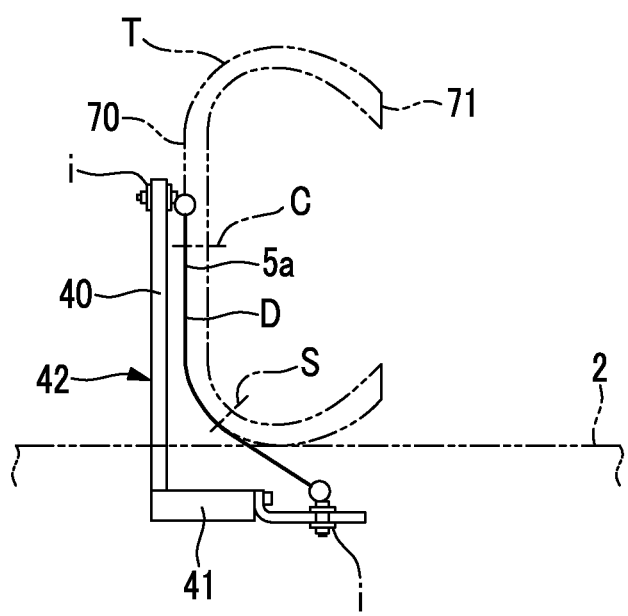
FIG. 4B is a front view of the outer-peripheral-side measuring tip in the first modification example of the embodiment of the invention, in a state where the outer-peripheral-side measuring tip has been pressed against the tire.

For example, a case where the coil spring B is used as the outer-peripheral-side measuring tip 5a has been described in the above-described embodiment. However, the outer-peripheral-side measuring tip may be curvedly deformable along the tire shape from the center portion C of the tread portion 70 to the shoulder portion S thereof in the width direction of the tire T without being limited to the coil springs. For example, as a first modification example, as shown in FIGS. 4A and 4B, a linear electric conductor D having flexibility may be used as the outer-peripheral-side measuring tip 5a. Also in the case shown in FIGS. 4A and 4B, similar to the above-described embodiment, the outer-peripheral-side measuring tip 5a becomes curvedly deformable along the outer shape of the tread portion 70 by pressing the tire T thereagainst. As the linear electric conductors D, steel wires having flexibility, wires, and threads having conductivity at least on a surface thereof, and the like can be used.

Figure 5:
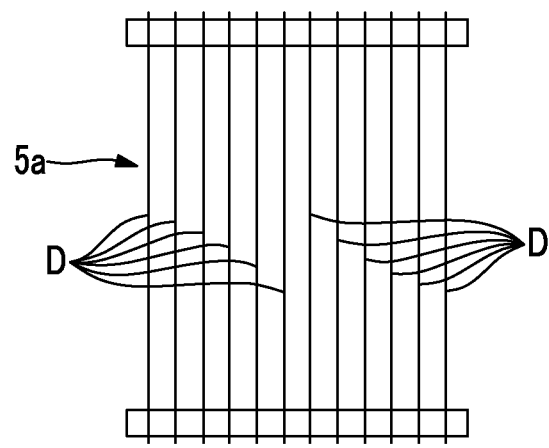
FIG. 5 is a plan view showing an outer-peripheral-side measuring tip in a second modification example of the embodiment of the invention.

Moreover, as a second modification example, as shown in FIG. 5, a plurality of linear electric conductors D having flexibility may be arranged side by side in the circumferential direction of the tire T. Additionally, the electric conductors D used for the outer-peripheral-side measuring tip 5a may be sheet-like electric conductors without being limited to the linear conductors.

Figure 6A:
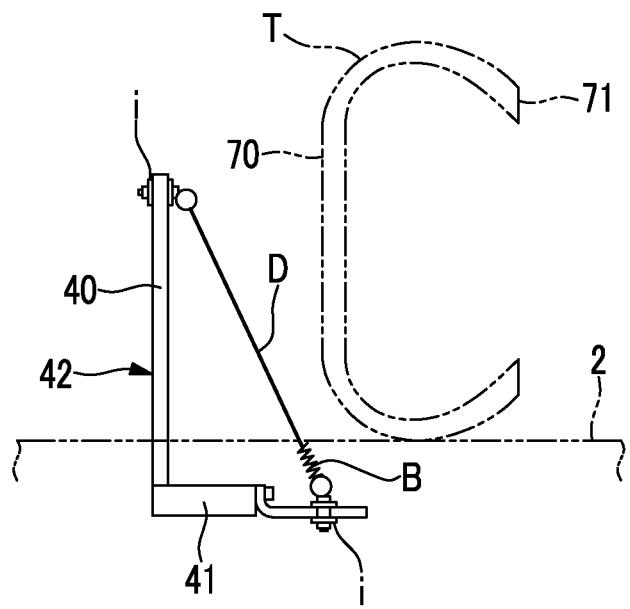
FIG. 6A is a front view equivalent to FIG. 4A in a third modification example of the embodiment of the invention, in a state before an outer-peripheral-side measuring tip is pressed against a tire.
Figure 6B:
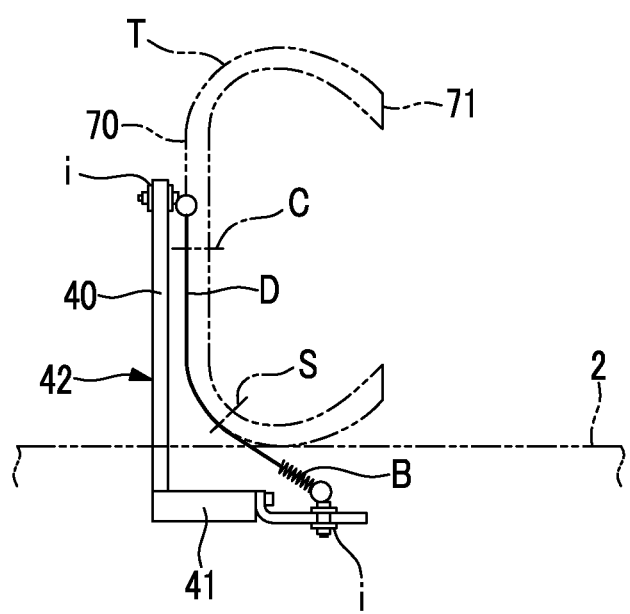
FIG. 6B is a front view equivalent to FIG. 4B in the third modification example of the embodiment of the invention, in a state where the outer-peripheral-side measuring tip has been pressed against the tire.

Additionally, in the above-described embodiment, a case where the coil spring B is used has been described as an example in order to give elasticity to the outer-peripheral-side measuring tip 5a. However, a conductive material that is elastically deformable and has elasticity is not limited to the coil spring B. Additionally, for example, as a third modification example, as shown in FIGS. 6A and 6B, a conductive material, such as a coil spring B, which is elastically deformable and has elasticity, may be interposed in a portion of an electric conductor D.

Figure 7A:
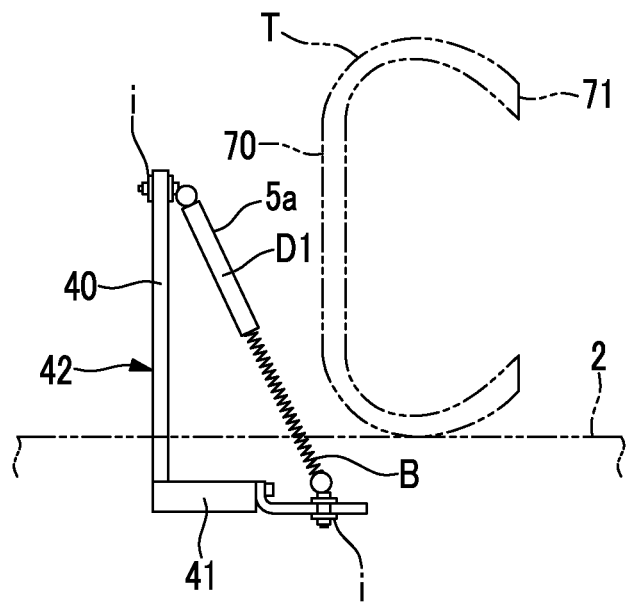
FIG. 7A is a front view equivalent to FIG. 4A in a fourth modification example of the embodiment of the invention, in a state before an outer-peripheral-side measuring tip is pressed against a tire.
Figure 7B:
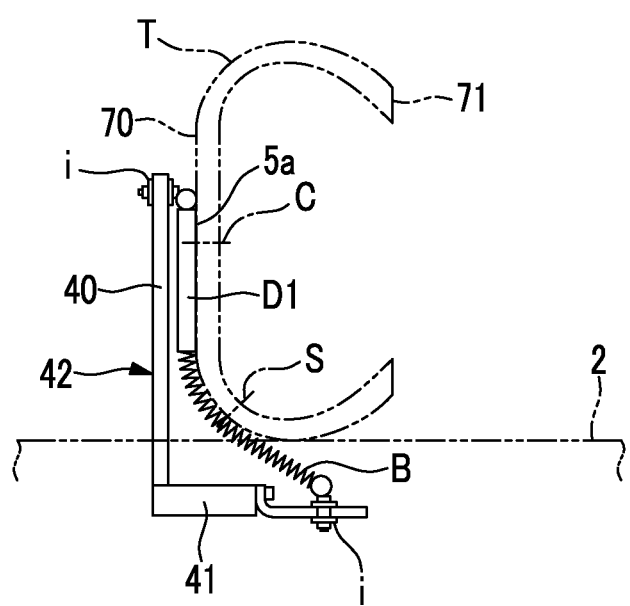
FIG. 7B is a front view equivalent to FIG. 4B in the fourth modification example of the embodiment of the invention, in a state where the outer-peripheral-side measuring tip has been pressed against the tire.

Moreover, although a case where the outer-peripheral-side measuring tip 5a is made curvable as a whole has been described as the embodiment and the respective modification examples, the outer-peripheral-side measuring tip may be made partially deformable and curvable. Specifically, as a fourth modification example, as shown in FIG. 7A, a coil spring B may be provided on a transverse frame 41 side, and a rod-shaped electric conductor D1 that is not deflected and deformed may be provided on a longitudinal frame 40 side. In this way, as shown in FIG. 7B, the electric conductor D1 abuts against a planar section near the center portion C of the tread portion 70, and the coil spring B is curved and deformed, and abuts against the shoulder portion S. As a result, it is possible to bring the outer-peripheral-side measuring tip 5a into elastic contact with at least the range from the center portion C of the tread portion 70 to the shoulder portion S thereof. In FIGS. 7A and 7B, a case where the coil spring B is used for the transverse frame 41 side has been described. However, the above-described linear electric conductor D having flexibility may be used instead of the coil spring B.

Figure 8A:
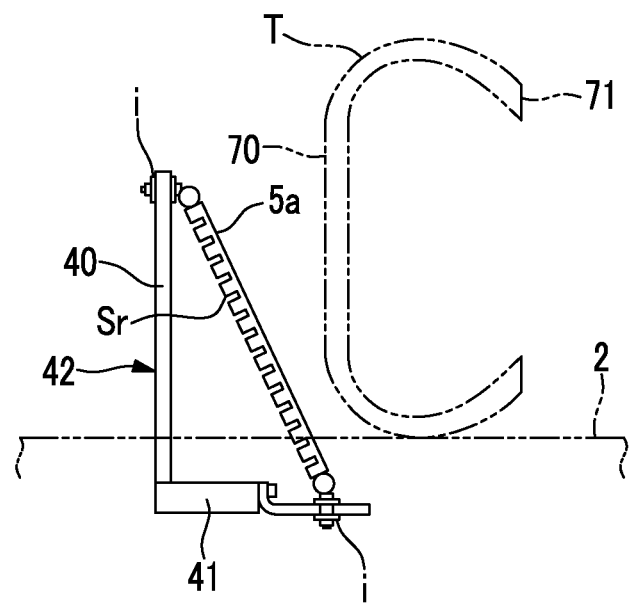
FIG. 8A is a front view equivalent to FIG. 4A in a fifth modification example of the embodiment of the invention, in a state before an outer-peripheral-side measuring tip is pressed against a tire.
Figure 8B:
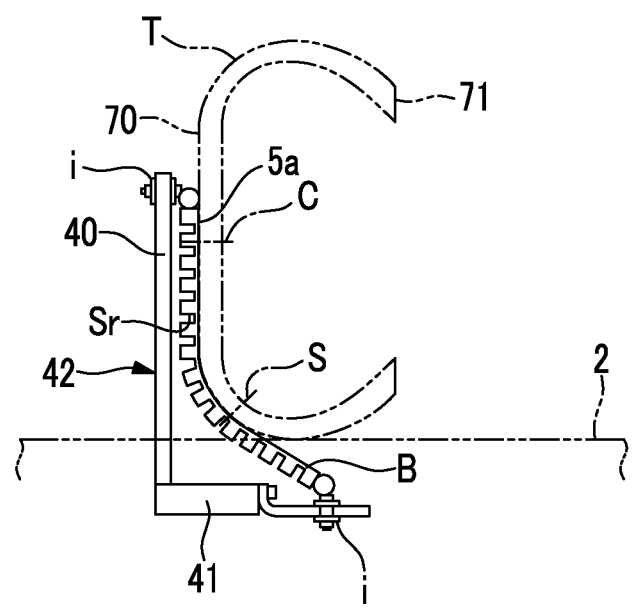
FIG. 8B is a front view equivalent to FIG. 4B in the fifth modification example of the embodiment of the invention, in a state where the outer-peripheral-side measuring tip has been pressed against the tire.

Additionally, cases where the outer-peripheral-side measuring tips 5a are the linear, sheet-like, and coiled electric conductors have been described in the above-described embodiment and respective modification examples. However, as a fifth modification example, as shown in FIGS. 8A and 8B, a plate-shaped electric conductor D2 may be used in which a plurality of slits Sr extending along the circumferential direction of the tire T are formed side by side at predetermined intervals in a length direction on a surface of the electric conductor opposite to a surface that comes into contact with the tire T. Similar to the outer-peripheral-side measuring tips 5a of the above-described embodiment and respective modification examples, the outer-peripheral-side measuring tip 5a including the electric conductor D2 is also curvedly deformable. Therefore, the outer-peripheral-side measuring tip can be stably brought into contact with at least the range from the center portion C of the tire T to the shoulder portion S thereof.

Moreover, in the above-described embodiment and respective modification examples, an example in which the upper end portion of the outer-peripheral-side measuring tip 5a is arranged at a position slightly higher than the center portion C of the tire T in the height direction has been described. However, the upper end portion of the outer-peripheral-side measuring tip 5a may be arranged at a position equal to or higher than the center portion C at the highest position in the center portion C of the tire T assumed as an object to be inspected.

Additionally, although an example in which two outer-peripheral-side measuring tips 5a each including the coil spring B are arranged side by side in the same direction has been described in the above-described embodiment, only one outer-peripheral-side measuring tip may be arranged. Additionally, although a case where only one inner-peripheral-side measuring tip 5b is arranged has been described, a plurality of the inner-peripheral-side measuring tips 5b may be provided side by side in the circumferential direction.

Moreover, although a case where the inner-peripheral-side measuring tip 5b is arranged in an inclined manner has been described in the above-described embodiment, the inner-peripheral-side measuring tip may be arranged so as to extend vertically upward, or the inclination angle thereof may be changed if necessary.

Additionally, although a case where the measuring tip unit 6 is displaced in the up-and-down direction by the lifting mechanism 12 has been described in the above-described embodiment, a direction in which the measuring tip unit 6 is displaced is not limited to the up-and-down direction, and may be a direction according to the posture during the conveyance of a tire T.

INDUSTRIAL APPLICABILITY

The invention can be widely applied to electrical resistance measuring devices for a tire that measure the electrical resistance from an inner peripheral portion of a tire to an outer peripheral portion thereof.

REFERENCE SIGNS LIST

5a: OUTER-PERIPHERAL-SIDE MEASURING TIP (MEASURING TIP)
5b: INNER-PERIPHERAL-SIDE MEASURING TIP (MEASURING TIP)
6: MEASURING TIP UNIT (MEASURING TIP SPACING ADJUSTING MECHANISM)
12: LIFTING MECHANISM (DISPLACEMENT MECHANISM)
70: TREAD PORTION (OUTER PERIPHERAL PORTION)
71: BEAD PORTION (INNER PERIPHERAL PORTION)
C: CENTER PORTION (CENTRAL PORTION)
S: SHOULDER PORTION
T: TIRE

The invention claimed is:

1. An electrical resistance measuring device for a tire that measures the electrical resistance from an inner peripheral portion of the tire to an outer peripheral portion thereof, the electrical resistance measuring device comprising:
a roller conveyor configured to convey the tire, the roller conveyor including rollers that are provided separately from each other on both sides of the roller conveyor in a width direction;
a measuring tip that is curvedly deformable along the shape of the tire, the measuring tip including:
an inner-peripheral-side measuring tip that is arranged on an inner peripheral side of the tire and is configured to contact the inner peripheral portion; and
an outer-peripheral-side measuring tip that is arranged on an outer peripheral side of the tire and is configured to contact the outer peripheral portion,
wherein
the outer-peripheral-side measuring tip is curvedly deformable along the shape of the tire from a central portion of the outer peripheral portion to a shoulder portion thereof in a width direction of the tire; and
the outer-peripheral-side measuring tip and the inner-peripheral-side measuring tip are allowed to protrude upward from between the rollers that are provided separately from each other on both sides of the roller conveyor in the width direction.

2. The electrical resistance measuring device for a tire according to claim 1,
wherein the outer-peripheral-side measuring tip is a linear electric conductor that is arranged to incline so that an upper portion is located further toward a radial outer side of the tire than a lower portion.

3. The electrical resistance measuring device for a tire according to claim 1,
wherein the outer-peripheral-side measuring tip is elastically deformable, and comes into contact with the outer peripheral portion in an elastically deformed state.

4. The electrical resistance measuring device for a tire according to claim 1,
wherein two of the outer-peripheral-side measuring tips and one of the inner-peripheral-side measuring tip are provided.

5. The electrical resistance measuring device for a tire according to claim 1, further comprising:
   a measuring tip spacing adjusting mechanism that creates the distance between the outer-peripheral-side measuring tip and the inner-peripheral-side measuring tip in a floating state.

6. The electrical resistance measuring device for a tire according to claim 1, further comprising:
   a displacement mechanism that displaces the outer-peripheral-side measuring tip and the inner-peripheral-side measuring tip so as to approach and separate from the tire.

* * * * *